United States Patent [19]

Hopson et al.

[11] Patent Number: 5,356,218
[45] Date of Patent: Oct. 18, 1994

[54] PROBE FOR PROVIDING SURFACE IMAGES

[75] Inventors: Theresa J. Hopson, Mesa; Ronald N. Legge, Scottsdale; Juan P. Carrejo, Tempe, all of Ariz.

[73] Assignee: Motorola, Inc., Schaumburg, Ill.

[21] Appl. No.: 55,887

[22] Filed: May 4, 1993

[51] Int. Cl.⁵ ............................. G01J 5/02; G01J 5/12
[52] U.S. Cl. .................................... 374/124; 374/137; 374/141; 250/330
[58] Field of Search ............... 374/124, 137, 179, 120, 374/141; 250/330

[56] References Cited

U.S. PATENT DOCUMENTS

| | | | |
|---|---|---|---|
| 3,262,315 | 7/1966 | Lux et al. | 374/179 |
| 3,477,122 | 11/1969 | Hamrick . | |
| 3,531,642 | 9/1970 | Barnes et al. | 374/124 |
| 3,930,159 | 12/1975 | Marquet | 374/124 |
| 4,112,362 | 9/1978 | Hower et al. | 374/137 |
| 4,360,277 | 11/1982 | Daniel et al. | 374/137 |
| 4,379,461 | 4/1983 | Nilsson et al. | 374/179 |
| 4,416,553 | 11/1983 | Huebscher | 374/179 |
| 4,747,698 | 5/1988 | Wickramasinghe et al. | 374/124 |
| 4,806,755 | 2/1989 | Duerig et al. . | |
| 4,941,753 | 7/1990 | Wickramasinghe | 374/137 |

FOREIGN PATENT DOCUMENTS

| | | | |
|---|---|---|---|
| 0094622 | 6/1982 | Japan | 374/179 |
| 0244825 | 12/1985 | Japan | 374/120 |
| 362139338 | 6/1987 | Japan | 374/179 |
| 8100764 | 3/1981 | World Int. Prop. O. | 374/124 |

OTHER PUBLICATIONS

C. C. Williams et al, "Scanning Thermal Profiler", Applied Physics Letter, vol. 49, No. 23, pp. 1587-1589, 1986.
Brochure "Microlevers", Park Scientific Instruments, Sunyvale, Calif. (no date).
Newsletter, "Nano Tips", Digital Instruments, Inc., vol. 1, Issue 2, Apr. 1989.
Newsletter, "Nano Tips", Digital Instruments, Inc., vol. 4, Issue 1, (no date).
Majumdar et al, "Thermal Imaging Using The Atomic Force Microscope", Presentation to American Vacuum Society, Nov. 9-13, 1992.
J. Carrejo et al, "Multi-Purpose Metal Cantilever Tip For Simultaneous AFM And Thermal Imaging", Technical Developments, Motorola, Inc., vol. 18, pp. 12-13, Mar., 1993.

*Primary Examiner*—Diego F. F. Gutierrez
*Attorney, Agent, or Firm*—Robert F. Hightower; Joe E. Barbee

[57] ABSTRACT

A probe (10,30,40) for forming images of surfaces (11) facilitates simultaneous formation of both thermal and atomic force microsocopy images. The probe (10,30,40) includes a heat sensing assembly (15) that has a heat sensing element (19,38,42). An electrically isolating and thermally conductive tip (22,48) projects from the heat sensing assembly. The probe (10) also has a reflective element (24) that is positioned between a first end of the heat sensing assembly (15) and the electrically isolating and thermally conductive tip (22).

7 Claims, 3 Drawing Sheets

5,356,218

PROBE FOR PROVIDING SURFACE IMAGES

BACKGROUND OF THE INVENTION

The present invention relates, in general, to probes that are used for forming images of surfaces, and more particularly, to a novel probe for producing thermal and atomic force microscopy images of a surface.

In the past, the semiconductor industry has used atomic force microscopy (AFM) to provide images of semiconductor device surfaces. One problem with prior AFM measurement apparatus and measuring techniques is the inability to provide thermal images of a surface. Often, semiconductor devices have minute defects. When power is applied to the device, a defect can result in overheating and eventual destruction of the semiconductor device. Prior AFM probes typically cannot identify such overheated areas. Additionally, prior AFM probes generally are not capable of correlating overheated areas to topographical surface features.

Accordingly, it is desirable to have an AFM probe that can simultaneously provide a thermal image and topographical image of a surface.

SUMMARY OF THE INVENTION

Briefly stated, the present invention includes a probe that facilitates forming images of surfaces. The probe includes a heat sensing assembly that has a heat sensing element. An electrically isolating and thermally conducting tip projects from the heat sensing assembly. The probe also has a reflective element that is positioned between a first end of the heat sensing assembly and the electrically isolating and thermally conducting tip.

A method of forming the probe is also included.

DETAILED DESCRIPTION OF THE DRAWINGS

Figure 1:
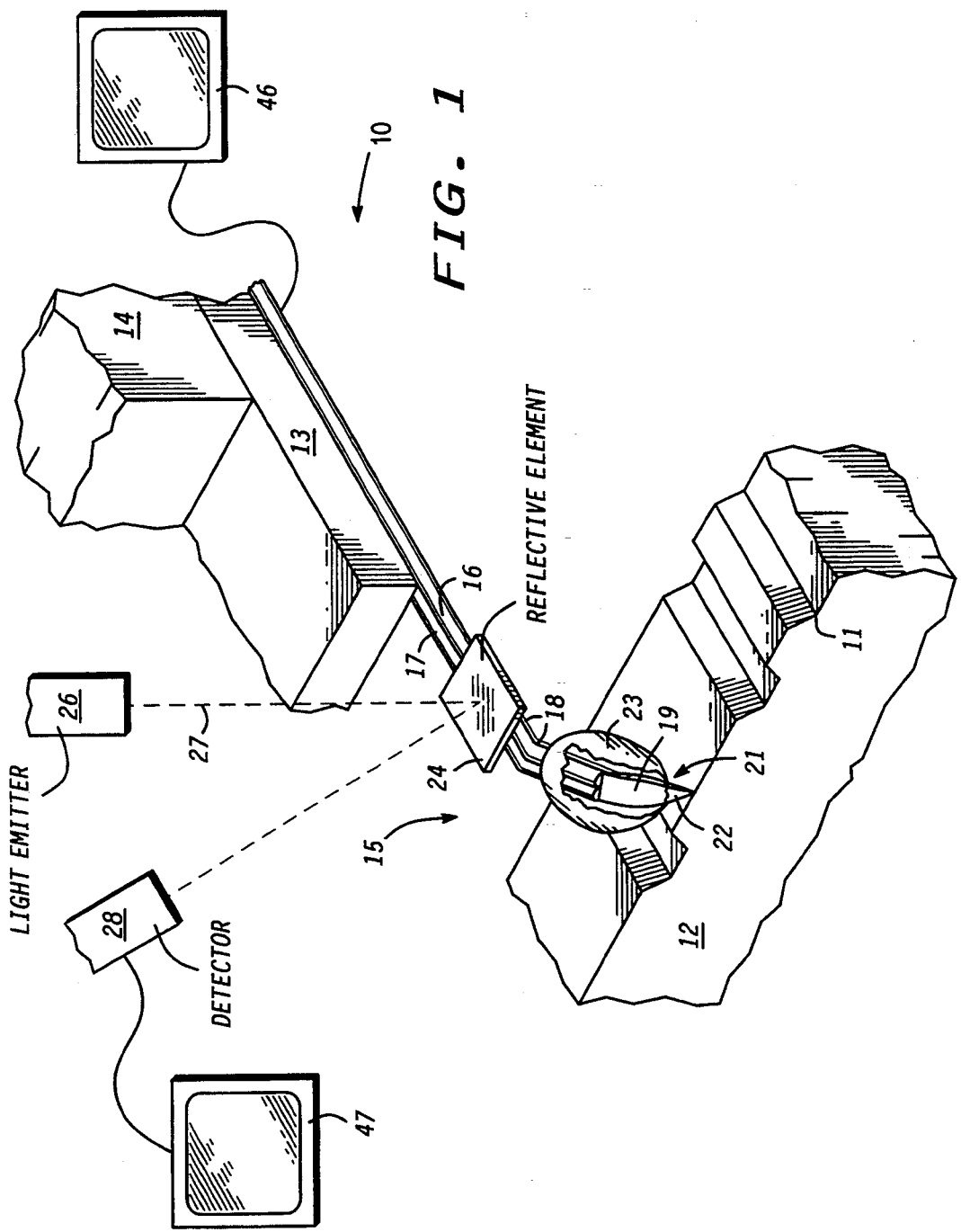
FIG. 1 illustrates an enlarged cut-away perspective view of a probe in accordance with the present invention.

FIG. 1 illustrates an enlarged perspective cut-away view of a thermal sensing atomic force microscopy (TAFM) probe 10. Probe 10 is capable of providing signals that facilitate simultaneous formation of both thermal and topographical images of a surface, such as a surface 11 of a semiconductor device 12. Probe 10 includes a heat sensing assembly or thermocouple assembly 15 that receives thermal energy from surface 11 and produces electrical signals representing the temperature of surface 11. A first end of assembly 15 is attached to a surface of a rigid support 13 in order to provide a stable reference for assembly 15 during thermal and AFM measurements. Generally, assembly 15 is positioned parallel to the surface of support 13 so that assembly 15 extends from support 13. The attachment should result in assembly 15 having a spring constant of approximately 0.5 to 15 newtons/meter. In the preferred embodiment, probe 10 has a spring constant of less than approximately 2.5 newtons/meter.

Assembly 15 includes a heat sensing element or thermocouple junction 19, a first thermocouple wire 16, and a second thermocouple wire 17. Wires 16 and 17 can be any of a variety of thermocouple metals or alloys that are well known to those skilled in the art. For example, either of wires 16 and 17 could be a platinum-rhodium alloy, a tungsten-rhenium alloy, or other materials that are capable of converting thermal energy into electrical signals. The materials chosen should have the largest voltage change per degree Celsius temperature change available. In the preferred embodiment, wires 16 and 17 provide a voltage change of approximately twenty to twenty-five millivolts per degree Celsius. Also in this preferred embodiment, wires 16 and 17 are two different alloys manufactured by Hoskins Manufacturing Co. of Detriot Mich. and known by trade names as Chromel and Alumel. Chromel is an alloy having approximately 90% nickel and 10% chromium, and Alumel is an alloy of approximately 95% nickel, 2.5% manganese, and 2.5% aluminum. The diameter of wires 16 and 17 should be sufficient to provide support yet small enough to provide high resolution thermal measurements. In the preferred embodiment, wires 16 and 17 have a diameter of approximately 15 to 75 microns. Smaller wire may be used, however, smaller wire is more difficult to handle. The wire size also affects the thermal measurement resolution of probe 10. The 75 micron diameter wire used in the preferred embodiment results in a capability of identifying a 0.25 degrees Celsius (°C.) temperature difference between two points approximately one micron apart.

Thermocouple junction 19 is formed by spot welding an end of wire 16 to an end of wire 17. A flat spot or mounting platform 21 is formed on the end of junction 19 in order to receive a tip 22. Platform 21 is formed by removing the extreme end of junction 19. In the preferred embodiment, a pair of model number 5210 scissors manufactured by Cutrite Inc. of Syracuse N.Y. is used to cut-off a portion of junction 19 and provide a smooth flat area that serves as platform 21.

In the preferred embodiment, tip 22 is a diamond shard that is positioned on platform 21. The diamond shard is used because it is both electrically isolating and thermally conducting. The electrically insulating characteristic facilitates utilizing probe 10 on electrically conducting surfaces as well as electrically insulating surfaces. In order to ensure high thermal conductivity, it is important that the diamond shard substantially contacts junction 19. There should be no contamination or adhesive between the diamond shard and platform 21. An external adhesive 23 is used to attach the diamond shard to junction 19 in order to prevent having adhesive between the diamond shard and junction 19. Adhesive 23 is shown partially cut-away in order to better show junction 19 and platform 21. Adhesive 23 surrounds the outside of junction 19 and a portion of the outside of the diamond shard thereby attaching the diamond shard to wires 16 and 17. It has been found that wetting adhesive 23 first to wires 16 and 17 allows surface tension to form adhesive 23 into a somewhat spherically shaped mass that slightly overlaps the edge of the diamond shard. This overlap attaches the outside of the diamond shard to wires 16 and 17. The attachment is facilitated by having the diamond shard's base approximately equal the combined diameters of wires 16 and 17. The mass of adhesive 23 also isolates the body of junction 19 from the heat of surface 11 thereby ensuring that junction 19 responds to temperatures transmitted through tip 22. An example of one suitable adhesive that can be used for adhesive 23 is an epoxy manufactured by the Dexter Corporation of Seabrook N.J. under the trademark "EPOXI-PATCH".

In order to ensure that tip 22 is substantially perpendicular to surface 11, assembly 15 has a bend 18 that is located between support 13 and tip 22. Bend 18 has an angle that is sufficient to ensure that tip 22 is substantially perpendicular to surface 11. In the preferred embodiment, bend 18 is located approximately 1000 to 1500 microns from support 13. Also in the preferred embodiment, tip 22 projects approximately 400 to 500 microns from the plane that includes the surface of support 13.

Probe 10 also includes a reflective element 24 that is utilized to provide atomic force microscopy (AFM) images of surface 11. Element 24 is positioned on assembly 15 at a location between bend 18 and support 13. Element 24 should be as close to bend 18 as possible in order to maximize resolution. In the preferred embodiment, the center of element 24 is approximately 500 to 700 microns from support 13. Light, illustrated by a dashed line 27, is emitted from a light emitter 26. A laser is an example of one suitable embodiment of emitter 26. The light strikes element 24 and is reflected to a detector 28 which converts the light to electrical signals. In the preferred embodiment, element 24 is a piece of aluminum foil that is attached to wires 16 and 17. In this preferred embodiment, it is important to use an insulator to attach the aluminum foil to wires 16 and 17 in order to prevent forming an electrical short between wires 16 and 17.

In operation, operating power is applied to semiconductor device 12 so that surface 11 may reach normal operating temperature. Probe 10 is used in the constant force mode to ensure that tip 22 maintains contact with surface 11. As probe 10 is moved along surface 11, element 19 converts the thermal energy from surface 11 to electrical signals that are displayed as a thermal image of surface 11 on a thermal display device 46. Simultaneously, AFM signals from detector 28 are displayed as a topographical image of surface 11 on an AFM display device 47. In the preferred embodiment, displays 46 and 47 are portions of a Nanoscope III Atomic Force Microscope manufactured by Digital Instruments Inc. of Santa Barbara Calif. Simultaneously displaying the thermal and AFM images allows detecting overheated areas of surface 11 by using the thermal display of device 46, and correlating the overheated areas to physical structures on surface 11 by using the topographical image on device 47.

Figure 2:
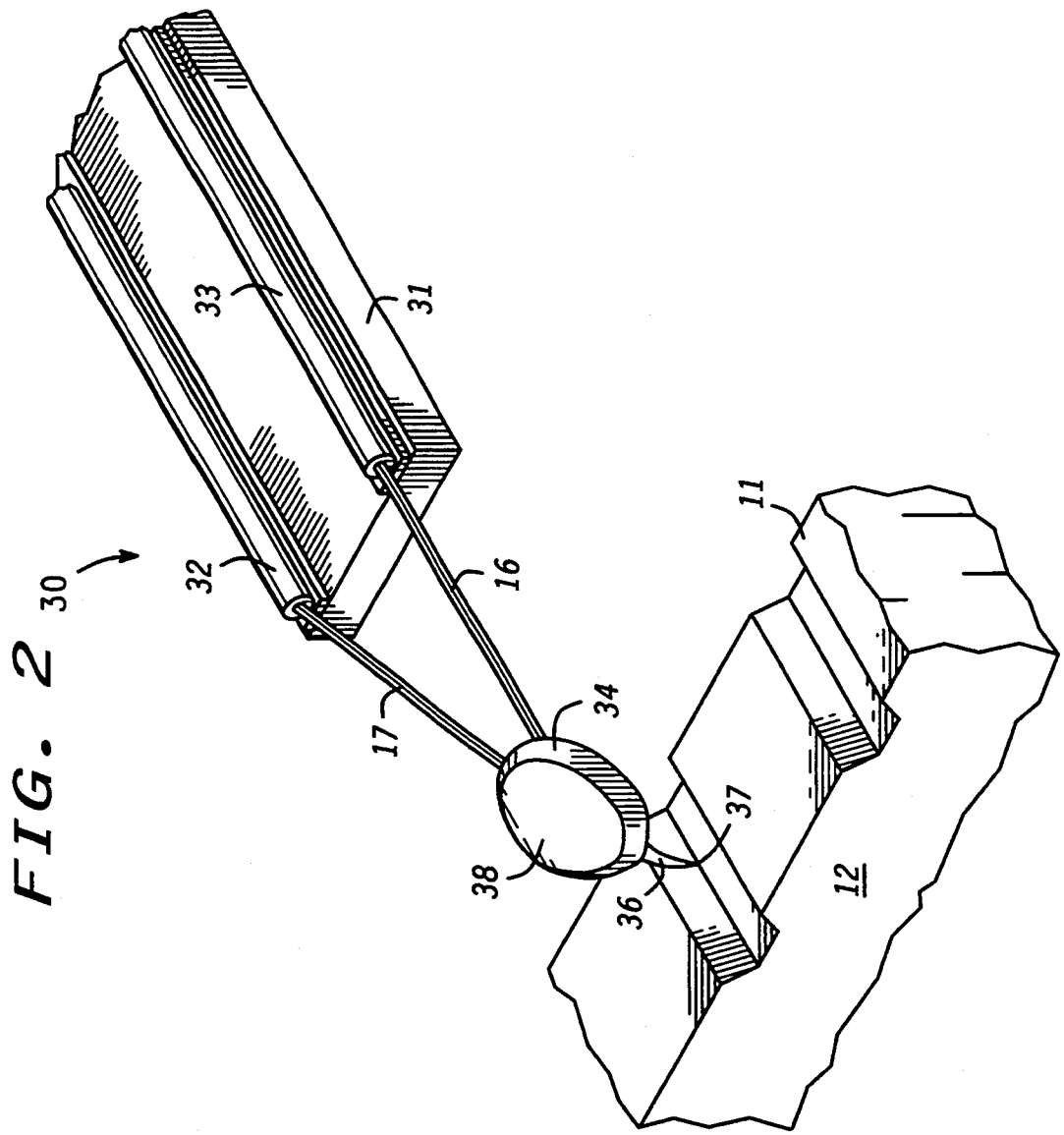
FIG. 2 illustrates an enlarged perspective view of an alternate embodiment of a probe in accordance with the present invention.

FIG. 2 illustrates an enlarged perspective view of an alternate embodiment of a TAFM probe 30 that facilitates simultaneous thermal and AFM imaging of surface 11. Elements of FIG. 2 that are the same as FIG. 1 have the same reference numerals. Probe 30 includes a rigid support 31 that functions to support wires 16 and 17. Support 31 includes a first conductor 32 and a second conductor 33 that provide electrical connection to thermal display device 46 (see FIG. 1). Support 31 is a printed circuit board having conductors 32 and 33 formed on a surface of support 31 by techniques that are well known to those skilled in the art of producing printed circuit boards. It is important that conductors 32 and 33 are formed from the same material in order to prevent formation of dissimilar thermal junctions between conductors 32 and 33, and wires 16 and 17. Such dissimilar thermal junctions would result in erroneous measurements of temperatures on surface 11.

A first end of wire 17 is attached to conductor 32 by utilizing a wire bonder that is typically used for bonding wires to semiconductor devices. An example of such a wire bonder is a Mech-E1 model No. 909 from Marpet Enterprises Inc. of Wakefield Md. Wire 17 is formed to have a length sufficient to extend from conductor 32 to a tip 37. In the preferred embodiment, wire 17 has a length of at least approximately 1500 microns. The wire bonder is also used to attach a first end of wire 16 to conductor 33. A second end of wire 16 is attached to wire 17 by the wire bonder in order to form a thermocouple junction 34. By wire bonding wire 16 to wire 17, a portion of junction 34 forms a reflective surface or reflective element 38 that functions similarly to reflective element 24 shown in FIG. 1. It has been found that bonding a Chromel wire to an Alumel wire provides a specular reflective element.

A second end of wire 17 is cut at an angle in order to form a sharp tip 37. The model 5210 scissors described in the discussion of FIG. 1 are used to cut wire 17. The resulting tip 37 has a radius of curvature of approximately two to six microns which facilitates the high resolution of probe 30. A portion of wire 17 extending from junction 34 toward tip 37 is bent at an angle so that tip 37 is substantially perpendicular to surface 11. An electrically insulating tip, such as tip 22 (see FIG. 1), could be attached to the second end of wire 17 by the means described in the discussion of FIG. 1. In addition, the method of using wire bonding to form a thermocouple junction could be used to form thermocouple junction 19 that is shown in FIG. 1.

Tip 37 can also be made electrically insulating by using electron beam contamination deposition. Electron beam contamination deposition is a technique of growing sharp insulating projections from the surface of objects. One example of such a deposition technique is disclosed in the newsletter Nano Tips, *The Journal for Nanoscope Users*, Vol. 4, Issue 1, 1992, p. 2. Electrically insulating tip 37 facilitates using probe 30 on electrically insulating and electrically conducting surfaces.

Figure 3:
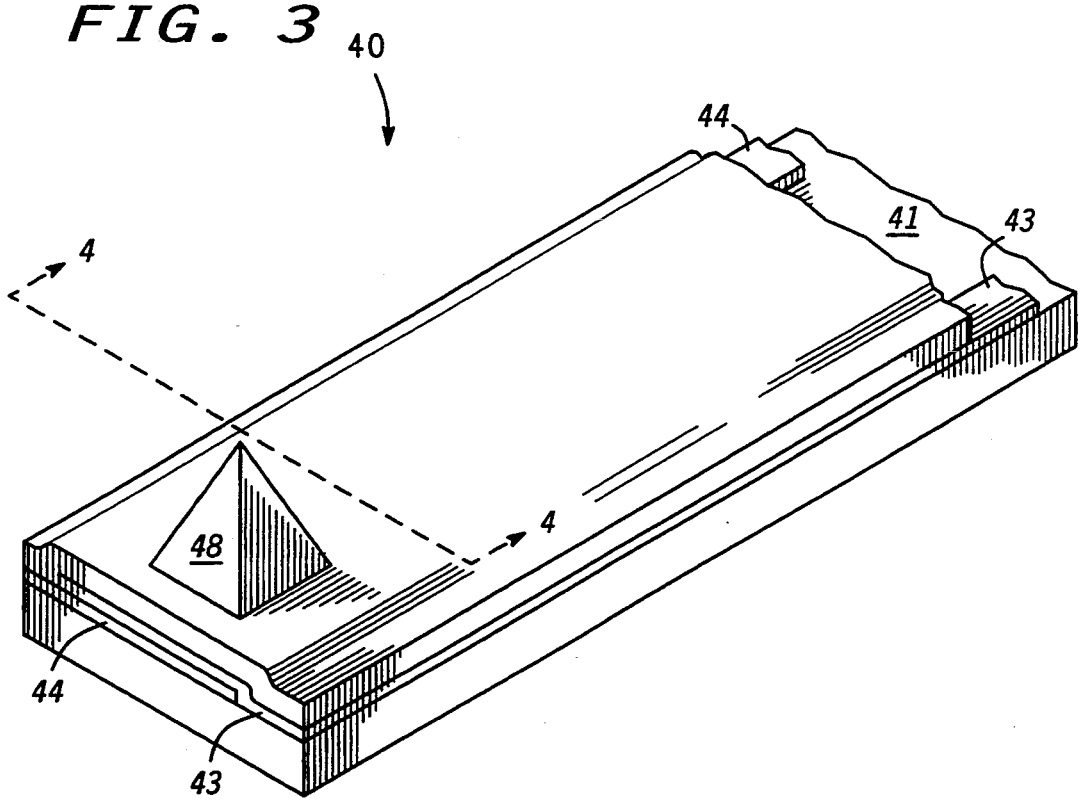
FIG. 3 illustrates an enlarged perspective view of another embodiment of a probe in accordance with the present invention.
Figure 4:
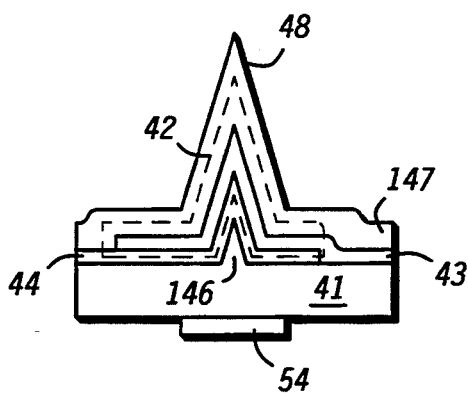
FIG. 4 illustrates an enlarged cross-section of a portion of the probe of FIG. 3.

FIG. 3 illustrates a perspective view of a portion of an alternate embodiment of a TAFM probe 40. FIG. 4 illustrates an enlarged cross-section along line 4—4 of probe 40 shown in FIG. 3. The discussion of FIG. 3 requires referencing both FIG. 3 and FIG. 4. Consequently, the discussion of FIG. 3 and FIG. 4 are combined. Probe 40 includes a flexible cantilever 41 having a sharply pointed projection 146 that is utilized for performing AFM measurements. As shown in FIG. 4, projection 146 is covered by other portions of probe 40, thus, projection 146 is not separately visible in FIG. 3. A first end of cantilever 41 is generally attached to a rigid support such as support 13 shown in FIG. 1. Projection 146 is positioned on a bottom surface near a second end of cantilever 41. Cantilever 41 is generally a rectangular bar of a material that has sufficient flexibility to provide a spring constant of approximately 0.5 to 15 newtons/meter. Typically, cantilever 41 is approximately 75 to 250 microns long and approximately 0.5 to 6.0 microns thick. In the preferred embodiment, cantilever 41 is a silicon or silicon nitride bar. A reflective element 54 generally is positioned on a top surface in order to facilitate AFM measurements. One example of a cantilever with a sharply pointed projection is disclosed in U.S. Pat. No. 4,806,705 issued to Urs. T. Duerig on Feb. 21, 1989 which is hereby incorporated herein by reference. An additional example of a cantilever with a sharply pointed projection is available under the trademark of "Microlever" from Park Scientific Instruments of Sunnyvale Calif.

In addition to cantilever 41 and projection 146, probe 40 also includes a heat sensing element or thermocouple junction 42 that is formed on projection 146. Junction 42 is substantially enclosed by a dashed outline that is shown in FIG. 4. As shown in FIG. 3 and FIG. 4, junction 42 is formed by applying a first thermocouple conductor 44 on a portion of the bottom surface of cantilever 41 so that conductor 44 covers projection 146. A second thermocouple conductor 43 is applied to cover the portion of conductor 44 that is on projection 146. Additionally, conductor 43 extends along the surface of cantilever 41 and is generally parallel to conductor 44. Conductors 44 and 43 are applied by sputtering, evaporation, or other techniques that are well known to those skilled in the semiconductor art. Because of the high temperatures used in applying conductor 43, the portion of conductor 43 that covers conductor 44 forms thermocouple junction 42 covering projection 146. In the preferred embodiment, conductors 43 and 44 are sputtered onto cantilever 41. Although sputtering is a low temperature process, the sputtering plasma heats probe 40 sufficiently to create thermocouple junction 42. Subsequently, junction 42 is covered with an insulator 147 such as silicon dioxide, silicon nitride, or diamond. A portion of insulator 147 that covers junction 42 forms a thermally conducting and electrically insulating tip 48 similar to tip 22 shown in FIG. 1.

Conductors 43 and 44 also provide electrical connection to the circuitry of thermal display device 46 shown in FIG. 1. Consequently, cantilever 41, projection 146, junction 42, and conductors 43 and 44 function as a heat sensing assembly similar to assembly 15 shown in FIG. 1.

By now it should be appreciated that there has been provided a novel thermal sensing AFM (TAFM) probe that provides both thermal and topographical images of a surface. Simultaneously producing both thermal and AFM images allow correlating hot spots detected by the thermal image directly to physical structures or defects on the surface. Positioning heat sensing element 19 near the surface to be imaged ensures accurate thermal measurements. Forming reflective surface 24 on heat sensing assembly 15 facilitates performing thermal and AFM measurements simultaneously. Utilizing an electrically insulating tip facilitates performing measurements on both electrically conducting and electrically insulating surfaces. Using a diamond tip also provides durability that results in a long probe lifetime.

We claim:

1. A probe for providing surface images comprising:
   a heat sensing assembly having a first end, a second end, and a heat sensing element;
   an electrically insulating and thermally conducting tip projecting from the heat sensing assembly; and
   a reflective element positioned between the first end of the heat sensing assembly and the electrically isolating and thermally conductive tip, wherein the reflective element cooperates with a light emitter and a detector to provide a first surface image, and wherein said heat sensing assembly and said electrically isolating and thermally conductive tip are used in providing a second surface image.

2. The probe of claim 1 wherein the heat sensing element is a thermocouple junction.

3. The probe of claim 1 further including the first end of the heat sensing assembly attached to a rigid support.

4. The probe of claim 1 further including a bend in the heat sensing assembly wherein the bend is located between the first end of the heat sensing assembly and the electrically insulating and thermally conducting tip, and wherein the electrically insulating and thermally conducting tip projects away from a plane that includes the first end of the heat sensing assembly.

5. The probe of claim 1 wherein the reflective element is a reflective portion of the heat sensing element.

6. The probe of claim 1 wherein the electrically insulating and thermally conducting tip includes a diamond shard attached to the heat sensing element.

7. The probe of claim 1 wherein the heat sensing assembly includes a flexible cantilever having a first thermocouple conductor and a second thermocouple conductor on a surface of the cantilever and wherein a portion of the second thermocouple conductor covers a portion of the first thermocouple conductor in order to form a thermocouple junction for said heat sensing element.

* * * * *